United States Patent
Tonomura et al.

(10) Patent No.: US 9,233,988 B2
(45) Date of Patent: Jan. 12, 2016

(54) SILYL-PROTECTED NITROGEN-CONTAINING CYCLIC COMPOUNDS AND MAKING METHOD

(71) Applicant: Shin-Etsu Chemical Co., Ltd., Tokyo (JP)

(72) Inventors: Yoichi Tonomura, Joetsu (JP); Tohru Kubota, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/264,831

(22) Filed: Apr. 29, 2014

(65) Prior Publication Data

US 2014/0357862 A1    Dec. 4, 2014

(30) Foreign Application Priority Data

May 30, 2013    (JP) ................................ 2013-113846

(51) Int. Cl.

| C07F 7/10 | (2006.01) |
|---|---|
| C07D 239/04 | (2006.01) |
| C07D 241/04 | (2006.01) |
| C04B 24/00 | (2006.01) |

(52) U.S. Cl.
CPC . *C07F 7/10* (2013.01); *C04B 24/00* (2013.01); *C07D 239/04* (2013.01); *C07D 241/04* (2013.01)

(58) Field of Classification Search
CPC .... C07F 7/10; C07D 239/04; C07D 295/023; C07D 295/03
USPC ................................. 544/229, 242
See application file for complete search history.

(56) References Cited

U.S. PATENT DOCUMENTS

| 3,943,104 A | 3/1976 | Waddill |
|---|---|---|
| 4,800,222 A | 1/1989 | Waddill |
| 2005/0234254 A1 | 10/2005 | Tonomura et al. |

FOREIGN PATENT DOCUMENTS

JP    S50-69200    6/1975

OTHER PUBLICATIONS

Breed et al., "Reactions of Silanes with Pentaerythritol and Piperazine", Journal of Organic Chemistry, vol. 25, No. 10, Oct. 1960, pp. 1804-1806, XP-002729010.
Search Report dated Sep. 17, 2014 for European Application No. 14 16 6648.

*Primary Examiner* — Venkataraman Balasubramanian
(74) *Attorney, Agent, or Firm* — Birch, Stewart, Kolasch & Birch, LLP

(57) ABSTRACT

Silyl-protected nitrogen-containing cyclic compounds having formula (1) are provided wherein $R^1$, $R^2$ and $R^3$ each are a monovalent hydrocarbon group, $R^4$ and $R^5$ each are a divalent hydrocarbon group, $R^6$, $R^7$ and $R^8$ each are H or a monovalent hydrocarbon group. A is $-C(O)OR^9$ or $-C\equiv N$, $R^9$ is a monovalent hydrocarbon group, and a is 0 or 1. The compounds are added to polyurethane, polyester or polycarbonate resins to form one part type curable compositions for imparting stiffness, mechanical strength and transparency thereto.

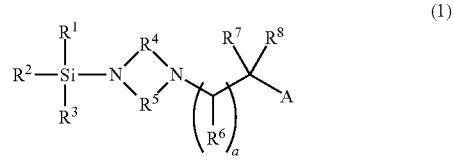

(1)

4 Claims, 8 Drawing Sheets

SILYL-PROTECTED NITROGEN-CONTAINING CYCLIC COMPOUNDS AND MAKING METHOD

CROSS-REFERENCE TO RELATED APPLICATION

This non-provisional application claims priority under 35 U.S.C. §119(a) on Patent Application No. 2013-113846 filed in Japan on May 30, 2013, the entire contents of which are hereby incorporated by reference.

TECHNICAL FIELD

This invention relates to silyl-protected nitrogen-containing cyclic compounds useful as resin additives, paint additives, adhesives and the like, and a method for preparing the same.

BACKGROUND ART

As described in Patent Documents 1 and 2, nitrogen-containing cyclic compounds, typically piperazine are useful as resin additives (specifically epoxy resin curing agents), paint additives, adhesives and the like. Since piperazine has a secondary amine structure, the use of piperazine as a curing agent for epoxy resins, for example, ensures that piperazine ring is introduced into the epoxy resin via reaction of the secondary amine moiety with an epoxy group, for thereby imparting the stiffness, mechanical strength and transparency (inclusive of the UV region) inherent to the piperazine ring structure to the epoxy resin.

However, a problem arises with the piperazine described in Patent Documents 1 and 2 because it has active hydrogen on the nitrogen atom. On use of piperazine as a curing agent for epoxy resins, if piperazine is previously added to an epoxy resin, viscosity buildup and gelation can occur with the lapse of time. It is not viable with a curable composition of one part type. The composition must be formulated as two part type which requires cumbersome operations like accurate weighing and mixing on use.

CITATION LIST

Patent Document 1: JP-A S50-69200 (U.S. Pat. No. 3,943,104)
Patent Document 2: U.S. Pat. No. 4,800,222

DISCLOSURE OF INVENTION

An object of the invention is to provide a compound which is added to polyurethane, polyester, polycarbonate or another resin to form a one part type composition for imparting stiffness, mechanical strength and transparency in the UV and visible regions thereto; and a method for preparing the same.

As alluded to previously, the piperazine described in Patent Documents 1 and 2 cannot be formulated as a one part type composition when used as a curing agent for epoxy resins. It would be contemplated to protect the active hydrogen on the nitrogen atom in piperazine with a silyl group such as trimethylsilyl. Such a silyl-protected piperazine can be previously added to epoxy resins or the like to form a one part type curable composition in that the composition is non-reactive and stable as long as water is shut off, but when contacted with water, hydrolysis takes place to induce deprotection whereby an amino group is regenerated so that the piperazine serves as a curing agent. Notably, the silyl-protected piperazine has an amino group as a sole functional group. The silyl-protected piperazine is fully effective for imparting stiffness, mechanical strength and transparency inclusive of the UV region when added to epoxy, acrylic and analogous resins, but less effective when added to polyurethane, polyester, polycarbonate and analogous resins having relatively weak interaction with amino groups.

The inventors have found that a silyl-protected nitrogen-containing cyclic compound having an ester or cyano group can be added to polyurethane, polyester, polycarbonate and analogous resins to form one part type curable compositions and is effective for impart stiffness, mechanical strength and transparency inclusive of the UV and visible regions thereto.

In one aspect, the invention provides a silyl-protected nitrogen-containing cyclic compound having the general formula (1).

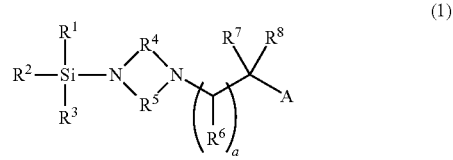

(1)

Herein $R^1$, $R^2$ and $R^3$ each are a substituted or unsubstituted monovalent hydrocarbon group of 1 to 20 carbon atoms, $R^4$ and $R^5$ each are a divalent hydrocarbon group of 1 to 10 carbon atoms, $R^6$, $R^7$ and $R^8$ each are hydrogen or a substituted or unsubstituted monovalent hydrocarbon group of 1 to 20 carbon atoms, A is —C(O)O$R^9$ or —C≡N, $R^9$ is a substituted or unsubstituted monovalent hydrocarbon group of 1 to 20 carbon atoms, and a is 0 or 1.

In a preferred embodiment, $R^4$ and $R^5$ each are ethylene.

In another aspect, the invention provides a method for preparing a silyl-protected nitrogen-containing cyclic compound, comprising the step of reacting a compound of the general formula (2):

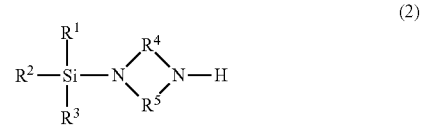

(2)

wherein $R^1$, $R^2$, $R^3$, $R^4$ and $R^5$ are as defined above, with a compound of the general formula (3):

(3)

wherein $R^{10}$ is hydrogen or a substituted or unsubstituted monovalent hydrocarbon group of 1 to 20 carbon atoms, A is as defined above, thereby forming a silyl-protected nitrogen-containing cyclic compound having the general formula (1a):

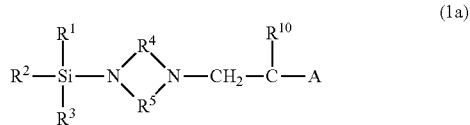

(1a)

wherein $R^1$, $R^2$, $R^3$, $R^4$, $R^5$, $R^{10}$, and A are as defined above.

In a further aspect, the invention provides a method for preparing a silyl-protected nitrogen-containing cyclic compound, comprising the step of silylating a nitrogen-containing cyclic compound of the general formula (4):

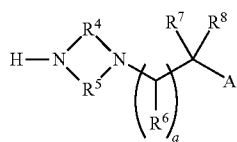
(4)

wherein $R^4$, $R^5$, $R^6$, $R^7$, $R^8$, A, and a are as defined above, with a silylating agent having $R^1R^2R^3Si$— group wherein $R^1$, $R^2$ and $R^3$ are as defined above, thereby forming a silyl-protected nitrogen-containing cyclic compound having the general formula (1):

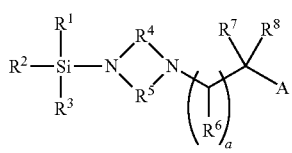
(1)

wherein $R^1$, $R^2$, $R^3$, $R^4$, $R^5$, $R^6$, $R^7$, $R^8$, A, and a are as defined above.

Advantageous Effects of Invention

When added to polyurethane, polyester, polycarbonate and analogous resins, the silyl-protected nitrogen-containing cyclic compounds of the invention are effective for imparting stiffness, mechanical strength and transparency inclusive of the UV and visible regions and can be formulated into one part type curable compositions. Thus the compounds are useful as resin additives, paint additives, and adhesives.

DESCRIPTION OF PREFERRED EMBODIMENTS

Figure 1:
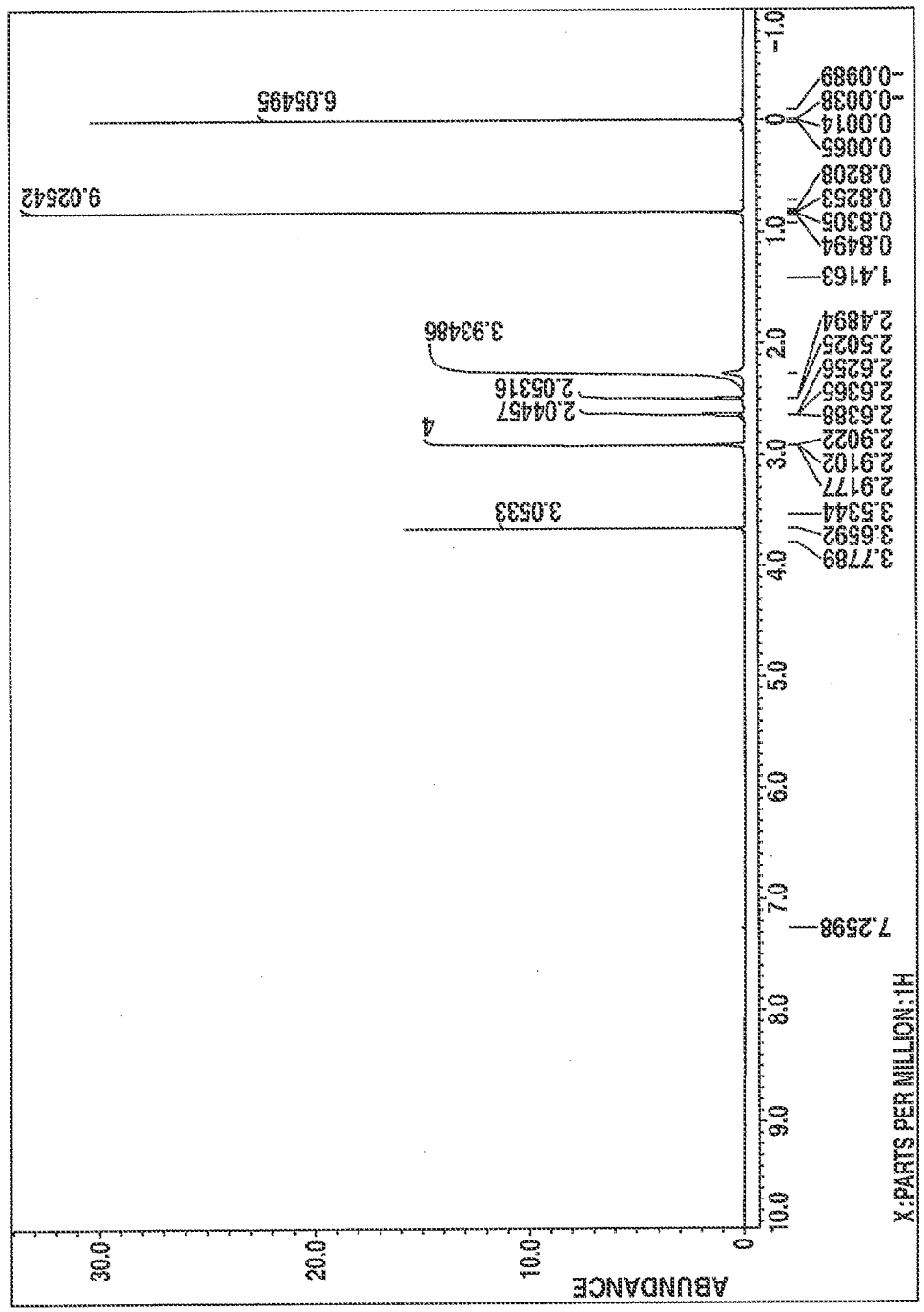
FIG. 1 is the $^1$H-NMR spectrum of 1-t-butyldimethylsilyl-4-(2-methoxycarbonylethyl)piperazine obtained in Example 1.

One embodiment of the invention is a silyl-protected nitrogen-containing cyclic compound having the general formula (1).

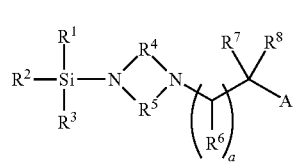
(1)

Herein $R^1$, $R^2$ and $R^3$ each are a substituted or unsubstituted monovalent hydrocarbon group of 1 to 20 carbon atoms, $R^4$ and $R^5$ each are a divalent hydrocarbon group of 1 to 10 carbon atoms, $R^6$, $R^7$ and $R^8$ each are hydrogen or a substituted or unsubstituted monovalent hydrocarbon group of 1 to 20 carbon atoms, A is —C(O)OR$^9$ or —C≡N, $R^9$ is a substituted or unsubstituted monovalent hydrocarbon group of 1 to 20 carbon atoms, and a is 0 or 1.

$R^1$, $R^2$, $R^3$ and $R^9$ each are selected from substituted or unsubstituted monovalent hydrocarbon groups of 1 to 20 carbon atoms, preferably 1 to 10 carbon atoms, and more preferably 1 to 5 carbon atoms, for example, straight, branched or cyclic alkyl, alkenyl, aryl, and aralkyl groups. Examples include straight alkyl groups such as methyl, ethyl, propyl, butyl, pentyl, hexyl, heptyl, octyl, decyl, dodecyl, tetradecyl, hexadecyl, octadecyl, and eicosyl; branched alkyl groups such as isopropyl, isobutyl, sec-butyl, tert-butyl, thexyl, and 2-ethylhexyl; cyclic alkyl groups such as cyclopentyl and cyclohexyl; alkenyl groups such as vinyl, allyl, and propenyl; aryl groups such as phenyl and tolyl; and aralkyl groups such as benzyl. Inter alia, methyl, ethyl, isopropyl, sec-butyl, and tert-butyl are preferred. In these hydrocarbon groups, some or all hydrogen atoms may be substituted by substituent groups. Suitable substituent groups include alkoxy groups such as methoxy, ethoxy, (iso)propoxy; halogen atoms such as fluorine, chlorine, bromine and iodine; cyano; amino; $C_6$-$C_{18}$ aryl groups such as phenyl and tolyl; $C_7$-$C_{18}$ aralkyl groups such as benzyl and phenethyl; $C_2$-$C_{10}$ acyl groups; trialkylsilyl, trialkoxysilyl, dialkylmonoalkoxysilyl or monoalkyldialkoxysilyl groups in which each alkyl or alkoxy moiety has 1 to 5 carbon atoms. Further, an ester (—COO—), ether (—O—), or sulfide (—S—) moiety may intervene in any of the foregoing groups. A combination of any two or more of the foregoing is also acceptable.

$R^4$ and $R^5$ each are selected from divalent hydrocarbon groups of 1 to 10 carbon atoms, preferably 1 to 5 carbon atoms, and more preferably 1 to 3 carbon atoms, for example, alkylene groups such as methylene, ethylene, trimethylene, tetramethylene, hexamethylene, octamethylene, decamethylene and isobutylene; arylene groups such as phenylene; and aralkylene groups such as methylenephenylene and methylenephenylenemethylene.

Preferred examples of the cyclic structure containing $R^4$ and $R^5$ are imidazolidine, piperazine, and hexahydropyrimidine structures. Inter alia, those compounds of formula (1) wherein both $R^4$ and $R^5$ are ethylene, that is, wherein the cyclic structure of the following formula:

is a piperazine structure, are preferred because they can impart high mechanical strength when added to resins.

$R^6$, $R^7$ and $R^8$ each are selected from hydrogen and substituted or unsubstituted monovalent hydrocarbon groups of 1 to 20 carbon atoms. Examples of the monovalent hydrocarbon groups are as illustrated above for $R^1$, $R^2$, and $R^3$. Inter alia, methyl, ethyl, isopropyl, sec-butyl and tert-butyl are preferred.

Illustrative, non-limiting examples of the silyl-protected nitrogen-containing cyclic compound having formula (1) include
1-trimethylsilyl-3-(2-methoxycarbonylethyl)imidazolidine,
1-hexyldimethylsilyl-3-(2-methoxycarbonylethyl)imidazolidine,
1-decyldimethylsilyl-3-(2-methoxycarbonylethyl)imidazolidine,
1-triethylsilyl-3-(2-methoxycarbonylethyl)imidazolidine,
1-triisobutylsilyl-3-(2-methoxycarbonylethyl)imidazolidine,
1-t-butyldimethylsilyl-3-(2-methoxycarbonylethyl)imidazolidine,
1-t-butyldiphenylsilyl-3-(2-methoxycarbonylethyl)imidazolidine,
1-thexyldimethylsilyl-3-(2-methoxycarbonylethyl)imidazolidine,
1-triisopropylsilyl-3-(2-methoxycarbonylethyl)imidazolidine,
1-tri(sec-butyl)silyl-3-(2-methoxycarbonylethyl)imidazolidine.
1-tricyclopentylsilyl-3-(2-methoxycarbonylethyl)imidazolidine,
1-tricyclohexylylsilyl-3-(2-methoxycarbonylethyl)imidazolidine,
1-trimethylsilyl-3-(2-ethoxycarbonylethyl)imidazolidine,
1-hexyldimethylsilyl-3-(2-ethoxycarbonylethyl)imidazolidine,
1-decyldimethylsilyl-3-(2-ethoxycarbonylethyl)imidazolidine,
1-triethylsilyl-3-(2-ethoxycarbonylethyl)imidazolidine,
1-triisobutylsilyl-3-(2-ethoxycarbonylethyl)imidazolidine,
1-t-butyldimethylsilyl-3-(2-ethoxycarbonylethyl)imidazolidine,
1-t-butyldiphenylsilyl-3-(2-ethoxycarbonylethyl)imidazolidine,
1-thexyldimethylsilyl-3-(2-ethoxycarbonylethyl)imidazolidine,
1-triisopropylsilyl-3-(2-ethoxycarbonylethyl)imidazolidine,
1-tri(sec-butyl)silyl-3-(2-ethoxycarbonylethyl)imidazolidine,
1-tricyclopentylsilyl-3-(2-ethoxycarbonylethyl)imidazolidine,
1-tricyclohexylylsilyl-3-(2-ethoxycarbonylethyl)imidazolidine,
1-trimethylsilyl-3-(2-methoxycarbonyl-2-methylethyl)imidazolidine,
1-hexyldimethylsilyl-3-(2-methoxycarbonyl-2-methylethyl)imidazolidine,
1-decyldimethylsilyl-3-(2-methoxycarbonyl-2-methylethyl)imidazolidine,
1-triethylsilyl-3-(2-methoxycarbonyl-2-methylethyl)imidazolidine,
1-triisobutylsilyl-3-(2-methoxycarbonyl-2-methylethyl)imidazolidine,
1-t-butyldimethylsilyl-3-(2-methoxycarbonyl-2-methylethyl)imidazolidine,
1-t-butyldiphenylsilyl-3-(2-methoxycarbonyl-2-methylethyl)imidazolidine,
1-thexyldimethylsilyl-3-(2-methoxycarbonyl-2-methylethyl)imidazolidine,
1-triisopropylsilyl-3-(2-methoxycarbonyl-2-methylethyl)imidazolidine,
1-tri(sec-butyl)silyl-3-(2-methoxycarbonyl-2-methylethyl)imidazolidine,
1-tricyclopentylsilyl-3-(2-methoxycarbonyl-2-methylethyl)imidazolidine,
1-tricyclohexylylsilyl-3-(2-methoxycarbonyl-2-methylethyl)imidazolidine,
1-trimethylsilyl-3-(2-ethoxycarbonyl-2-methylethyl)imidazolidine,
1-hexyldimethylsilyl-3-(2-ethoxycarbonyl-2-methylethyl)imidazolidine,
1-decyldimethylsilyl-3-(2-ethoxycarbonyl-2-methylethyl)imidazolidine,
1-triethylsilyl-3-(2-ethoxycarbonyl-2-methylethyl)imidazolidine,
1-triisobutylsilyl-3-(2-ethoxycarbonyl-2-methylethyl)imidazolidine,
1-t-butyldimethylsilyl-3-(2-ethoxycarbonyl-2-methylethyl)imidazolidine,
1-t-butyldiphenylsilyl-3-(2-ethoxycarbonyl-2-methylethyl)imidazolidine,
1-thexyldimethylsilyl-3-(2-ethoxycarbonyl-2-methylethyl)imidazolidine,
1-triisopropylsilyl-3-(2-ethoxycarbonyl-2-methylethyl)imidazolidine,
1-tri(sec-butyl)silyl-3-(2-ethoxycarbonyl-2-methylethyl)imidazolidine,
1-tricyclopentylsilyl-3-(2-ethoxycarbonyl-2-methylethyl)imidazolidine,
1-tricyclohexylylsilyl-3-(2-ethoxycarbonyl-2-methylethyl)imidazolidine,
1-trimethylsilyl-3-(2-cyanoethyl)imidazolidine,
1-hexyldimethylsilyl-3-(2-cyanoethyl)imidazolidine,
1-decyldimethylsilyl-3-(2-cyanoethyl)imidazolidine,
1-triethylsilyl-3-(2-cyanoethyl)imidazolidine,
1-triisobutylsilyl-3-(2-cyanoethyl)imidazolidine,
1-t-butyldimethylsilyl-3-(2-cyanoethyl)imidazolidine,
1-t-butyldiphenylsilyl-3-(2-cyanoethyl)imidazolidine,
1-thexyldimethylsilyl-3-(2-cyanoethyl)imidazolidine,
1-triisopropylsilyl-3-(2-cyanoethyl)imidazolidine,
1-tri(sec-butyl)silyl-3-(2-cyanoethyl)imidazolidine,
1-tricyclopentylsilyl-3-(2-cyanoethyl)imidazolidine,
1-tricyclohexylylsilyl-3-(2-cyanoethyl)imidazolidine,
1-trimethylsilyl-3-(2-cyano-2-methylethyl)imidazolidine,
1-hexyldimethylsilyl-3-(2-cyano-2-methylethyl)imidazolidine,
1-decyldimethylsilyl-3-(2-cyano-2-methylethyl)imidazolidine,
1-triethylsilyl-3-(2-cyano-2-methylethyl)imidazolidine,
1-triisobutylsilyl-3-(2-cyano-2-methylethyl)imidazolidine,
1-t-butyldimethylsilyl-3-(2-cyano-2-methylethyl)imidazolidine,
1-t-butyldiphenylsilyl-3-(2-cyano-2-methylethyl)imidazolidine,
1-thexyldimethylsilyl-3-(2-cyano-2-methylethyl)imidazolidine,
1-triisopropylsilyl-3-(2-cyano-2-methylethyl)imidazolidine,
1-tri(sec-butyl)silyl-3-(2-cyano-2-methylethyl)imidazolidine,
1-tricyclopentylsilyl-3-(2-cyano-2-methylethyl)imidazolidine,
1-tricyclohexylylsilyl-3-(2-cyano-2-methylethyl)imidazolidine,
1-trimethylsilyl-4-(2-methoxycarbonylethyl)piperazine,
1-hexyldimethylsilyl-4-(2-methoxycarbonylethyl)piperazine,
1-decyldimethylsilyl-4-(2-methoxycarbonylethyl)piperazine, 1-triethylsilyl-4-(2-methoxycarbonylethyl)piperazine,
1-triisobutylsilyl-4-(2-methoxycarbonylethyl)piperazine,
1-t-butyldimethylsilyl-4-(2-methoxycarbonylethyl)piperazine,
1-t-butyldiphenylsilyl-4-(2-methoxycarbonylethyl)piperazine,
1-thexyldimethylsilyl-4-(2-methoxycarbonylethyl)piperazine,
1-triisopropylsilyl-4-(2-methoxycarbonylethyl)piperazine,
1-tri(sec-butyl)silyl-4-(2-methoxycarbonylethyl)piperazine,
1-tricyclopentylsilyl-4-(2-methoxycarbonylethyl)piperazine,
1-tricyclohexylylsilyl-4-(2-methoxycarbonylethyl)piperazine,
1-trimethylsilyl-4-(2-ethoxycarbonylethyl)piperazine,
1-hexyldimethylsilyl-4-(2-ethoxycarbonylethyl)piperazine,
1-decyldimethylsilyl-4-(2-ethoxycarbonylethyl)piperazine,
1-triethylsilyl-4-(2-ethoxycarbonylethyl)piperazine,
1-triisobutylsilyl-4-(2-ethoxycarbonylethyl)piperazine,
1-t-butyldimethylsilyl-4-(2-ethoxycarbonylethyl)piperazine,
1-t-butyldiphenylsilyl-4-(2-ethoxycarbonylethyl)piperazine,
1-thexyldimethylsilyl-4-(2-ethoxycarbonylethyl)piperazine,
1-triisopropylsilyl-4-(2-ethoxycarbonylethyl)piperazine,
1-tri(sec-butyl)silyl-4-(2-ethoxycarbonylethyl)piperazine,
1-tricyclopentylsilyl-4-(2-ethoxycarbonylethyl)piperazine,
1-tricyclohexylylsilyl-4-(2-ethoxycarbonylethyl)piperazine,
1-trimethylsilyl-4-(2-methoxycarbonyl-2-methylethyl)piperazine,
1-hexyldimethylsilyl-4-(2-methoxycarbonyl-2-methylethyl)piperazine,
1-decyldimethylsilyl-4-(2-methoxycarbonyl-2-methylethyl)piperazine,
1-triethylsilyl-4-(2-methoxycarbonyl-2-methylethyl)piperazine,
1-triisobutylsilyl-4-(2-methoxycarbonyl-2-methylethyl)piperazine,
1-t-butyldimethylsilyl-4-(2-methoxycarbonyl-2-methylethyl)piperazine,
1-t-butyldiphenylsilyl-4-(2-methoxycarbonyl-2-methylethyl)piperazine,
1-thexyldimethylsilyl-4-(2-methoxycarbonyl-2-methylethyl)piperazine,
1-triisopropylsilyl-4-(2-methoxycarbonyl-2-methylethyl)piperazine,
1-tri(sec-butyl)silyl-4-(2-methoxycarbonyl-2-methylethyl)piperazine,
1-tricyclopentylsilyl-4-(2-methoxycarbonyl-2-methylethyl)piperazine,
1-tricyclohexylylsilyl-4-(2-methoxycarbonyl-2-methylethyl)piperazine,
1-trimethylsilyl-4-(2-ethoxycarbonyl-2-methylethyl)piperazine,
1-hexyldimethylsilyl-4-(2-ethoxycarbonyl-2-methylethyl)piperazine,
1-decyldimethylsilyl-4-(2-ethoxycarbonyl-2-methylethyl)piperazine,
1-triethylsilyl-4-(2-ethoxycarbonyl-2-methylethyl)piperazine,
1-triisobutylsilyl-4-(2-ethoxycarbonyl-2-methylethyl)piperazine,
1-t-butyldimethylsilyl-4-(2-ethoxycarbonyl-2-methylethyl)piperazine,
1-t-butyldiphenylsilyl-4-(2-ethoxycarbonyl-2-methylethyl)piperazine,
1-thexyldimethylsilyl-4-(2-ethoxycarbonyl-2-methylethyl)piperazine,
1-triisopropylsilyl-4-(2-ethoxycarbonyl-2-methylethyl)piperazine,
1-tri(sec-butyl)silyl-4-(2-ethoxycarbonyl-2-methylethyl)piperazine,
1-tricyclopentylsilyl-4-(2-ethoxycarbonyl-2-methylethyl)piperazine,
1-tricyclohexylylsilyl-4-(2-ethoxycarbonyl-2-methylethyl)piperazine,
1-trimethylsilyl-4-(2-cyanoethyl)piperazine,
1-hexyldimethylsilyl-4-(2-cyanoethyl)piperazine,
1-decyldimethylsilyl-4-(2-cyanoethyl)piperazine,
1-triethylsilyl-4-(2-cyanoethyl)piperazine,
1-triisobutylsilyl-4-(2-cyanoethyl)piperazine,
1-t-butyldimethylsilyl-4-(2-cyanoethyl)piperazine,
1-t-butyldiphenylsilyl-4-(2-cyanoethyl)piperazine,
1-thexyldimethylsilyl-4-(2-cyanoethyl)piperazine,
1-triisopropylsilyl-4-(2-cyanoethyl)piperazine,
1-tri(sec-butyl)silyl-4-(2-cyanoethyl)piperazine,
1-tricyclopentylsilyl-4-(2-cyanoethyl)piperazine,
1-tricyclohexylylsilyl-4-(2-cyanoethyl)piperazine,
1-trimethylsilyl-4-(2-cyano-2-methylethyl)piperazine,
1-hexyldimethylsilyl-4-(2-cyano-2-methylethyl)piperazine,
1-decyldimethylsilyl-4-(2-cyano-2-methylethyl)piperazine,
1-triethylsilyl-4-(2-cyano-2-methylethyl)piperazine,
1-triisobutylsilyl-4-(2-cyano-2-methylethyl)piperazine,
1-t-butyldimethylsilyl-4-(2-cyano-2-methylethyl)piperazine,
1-t-butyldiphenylsilyl-4-(2-cyano-2-methylethyl)piperazine,
1-thexyldimethylsilyl-4-(2-cyano-2-methylethyl)piperazine,
1-triisopropylsilyl-4-(2-cyano-2-methylethyl)piperazine,
1-tri(sec-butyl)silyl-4-(2-cyano-2-methylethyl)piperazine,
1-tricyclopentylsilyl-4-(2-cyano-2-methylethyl)piperazine,
1-tricyclohexylylsilyl-4-(2-cyano-2-methylethyl)piperazine,
1-trimethylsilyl-3-(2-methoxycarbonylethyl)hexahydropyrimidine,
1-hexyldimethylsilyl-3-(2-methoxycarbonylethyl)hexahydropyrimidine,
1-decyldimethylsilyl-3-(2-methoxycarbonylethyl)hexahydropyrimidine,
1-triethylsilyl-3-(2-methoxycarbonylethyl)hexahydropyrimidine,
1-triisobutylsilyl-3-(2-methoxycarbonylethyl)hexahydropyrimidine,
1-t-butyldimethylsilyl-3-(2-methoxycarbonylethyl)hexahydropyrimidine,
1-t-butyldiphenylsilyl-3-(2-methoxycarbonylethyl)hexahydropyrimidine,
1-thexyldimethylsilyl-3-(2-methoxycarbonylethyl)hexahydropyrimidine,
1-triisopropylsilyl-3-(2-methoxycarbonylethyl)hexahydropyrimidine,
1-tri(sec-butyl)silyl-3-(2-methoxycarbonylethyl)hexahydropyrimidine,
1-tricyclopentylsilyl-3-(2-methoxycarbonylethyl)hexahydropyrimidine,
1-tricyclohexylylsilyl-3-(2-methoxycarbonylethyl)hexahydropyrimidine,
1-trimethylsilyl-3-(2-ethoxycarbonylethyl)hexahydropyrimidine,
1-hexyldimethylsilyl-3-(2-ethoxycarbonylethyl)hexahydropyrimidine,
1-decyldimethylsilyl-3-(2-ethoxycarbonylethyl)hexahydropyrimidine,
1-triethylsilyl-3-(2-ethoxycarbonylethyl)hexahydropyrimidine, 1-triisobutylsilyl-3-(2-ethoxycarbonylethyl)hexahydropyrimidine,
1-t-butyldimethylsilyl-3-(2-ethoxycarbonylethyl)hexahydropyrimidine,
1-t-butyldiphenylsilyl-3-(2-ethoxycarbonylethyl)hexahydropyrimidine,
1-thexyldimethylsilyl-3-(2-ethoxycarbonylethyl)hexahydropyrimidine,
1-triisopropylsilyl-3-(2-ethoxycarbonylethyl)hexahydropyrimidine,
1-tri(sec-butyl)silyl-3-(2-ethoxycarbonylethyl)hexahydropyrimidine,
1-tricyclopentylsilyl-3-(2-ethoxycarbonylethyl)hexahydropyrimidine,
1-tricyclohexylylsilyl-3-(2-ethoxycarbonylethyl)hexahydropyrimidine,
1-trimethylsilyl-3-(2-methoxycarbonyl-2-methylethyl)hexahydropyrimidine,
1-hexyldimethylsilyl-3-(2-methoxycarbonyl-2-methylethyl)hexahydropyrimidine,
1-decyldimethylsilyl-3-(2-methoxycarbonyl-2-methylethyl)hexahydropyrimidine,
1-triethylsilyl-3-(2-methoxycarbonyl-2-methylethyl)hexahydropyrimidine,
1-triisobutylsilyl-3-(2-methoxycarbonyl-2-methylethyl)hexahydropyrimidine,
1-t-butyldimethylsilyl-3-(2-methoxycarbonyl-2-methylethyl)hexahydropyrimidine,
1-t-butyldiphenylsilyl-3-(2-methoxycarbonyl-2-methylethyl)hexahydropyrimidine,
1-thexyldimethylsilyl-3-(2-methoxycarbonyl-2-methylethyl)hexahydropyrimidine,
1-triisopropylsilyl-3-(2-methoxycarbonyl-2-methylethyl)hexahydropyrimidine,
1-tri(sec-butyl)silyl-3-(2-methoxycarbonyl-2-methylethyl)hexahydropyrimidine,
1-tricyclopentylsilyl-3-(2-methoxycarbonyl-2-methylethyl)hexahydropyrimidine,
1-tricyclohexylylsilyl-3-(2-methoxycarbonyl-2-methylethyl)hexahydropyrimidine,
1-trimethylsilyl-3-(2-ethoxycarbonyl-2-methylethyl)hexahydropyrimidine,
1-hexyldimethylsilyl-3-(2-ethoxycarbonyl-2-methylethyl)hexahydropyrimidine,
1-decyldimethylsilyl-3-(2-ethoxycarbonyl-2-methylethyl)hexahydropyrimidine,
1-triethylsilyl-3-(2-ethoxycarbonyl-2-methylethyl)hexahydropyrimidine,
1-triisobutylsilyl-3-(2-ethoxycarbonyl-2-methylethyl)hexahydropyrimidine,
1-t-butyldimethylsilyl-3-(2-ethoxycarbonyl-2-methylethyl)hexahydropyrimidine,
1-t-butyldiphenylsilyl-3-(2-ethoxycarbonyl-2-methylethyl)hexahydropyrimidine,
1-thexyldimethylsilyl-3-(2-ethoxycarbonyl-2-methylethyl)hexahydropyrimidine,
1-triisopropylsilyl-3-(2-ethoxycarbonyl-2-methylethyl)hexahydropyrimidine,
1-tri(sec-butyl)silyl-3-(2-ethoxycarbonyl-2-methylethyl)hexahydropyrimidine,
1-tricyclopentylsilyl-3-(2-ethoxycarbonyl-2-methylethyl)hexahydropyrimidine,
1-tricyclohexylylsilyl-3-(2-ethoxycarbonyl-2-methylethyl)hexahydropyrimidine,
1-trimethylsilyl-3-(2-cyanoethyl)hexahydropyrimidine,
1-hexyldimethylsilyl-3-(2-cyanoethyl)hexahydropyrimidine,
1-decyldimethylsilyl-3-(2-cyanoethyl)hexahydropyrimidine,
1-triethylsilyl-3-(2-cyanoethyl)hexahydropyrimidine,
1-triisobutylsilyl-3-(2-cyanoethyl)hexahydropyrimidine,
1-t-butyldimethylsilyl-3-(2-cyanoethyl)hexahydropyrimidine,
1-t-butyldiphenylsilyl-3-(2-cyanoethyl)hexahydropyrimidine,
1-thexyldimethylsilyl-3-(2-cyanoethyl)hexahydropyrimidine,
1-triisopropylsilyl-3-(2-cyanoethyl)hexahydropyrimidine,
1-tri(sec-butyl)silyl-3-(2-cyanoethyl)hexahydropyrimidine,
1-tricyclopentylsilyl-3-(2-cyanoethyl)hexahydropyrimidine,
1-tricyclohexylylsilyl-3-(2-cyanoethyl)hexahydropyrimidine,
1-trimethylsilyl-3-(2-cyano-2-methylethyl)hexahydropyrimidine,
1-hexyldimethylsilyl-3-(2-cyano-2-methylethyl)hexahydropyrimidine,
1-decyldimethylsilyl-3-(2-cyano-2-methylethyl)hexahydropyrimidine,
1-triethylsilyl-3-(2-cyano-2-methylethyl)hexahydropyrimidine,
1-triisobutylsilyl-3-(2-cyano-2-methylethyl)hexahydropyrimidine,
1-t-butyldimethylsilyl-3-(2-cyano-2-methylethyl)hexahydropyrimidine,
1-t-butyldiphenylsilyl-3-(2-cyano-2-methylethyl)hexahydropyrimidine,
1-thexyldimethylsilyl-3-(2-cyano-2-methylethyl)hexahydropyrimidine,
1-triisopropylsilyl-3-(2-cyano-2-methylethyl)hexahydropyrimidine,
1-tri(sec-butyl)silyl-3-(2-cyano-2-methylethyl)hexahydropyrimidine,
1-tricyclopentylsilyl-3-(2-cyano-2-methylethyl)hexahydropyrimidine,
1-tricyclohexylylsilyl-3-(2-cyano-2-methylethyl)hexahydropyrimidine, etc.

In another embodiment of the invention, the silyl-protected nitrogen-containing cyclic compound of formula (1) defined above may be prepared, for example, by reacting a compound of the general formula (2):

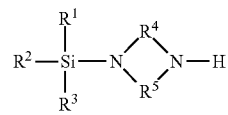

(2)

wherein $R^1$, $R^2$, $R^3$, $R^4$ and $R^5$ are as defined above, with a compound of the general formula (3):

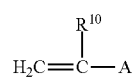

(3)

wherein $R^{10}$ is hydrogen or a substituted or unsubstituted monovalent hydrocarbon group of 1 to 20 carbon atoms, A is as defined above. In this embodiment, there is obtained a compound having the general formula (1a):

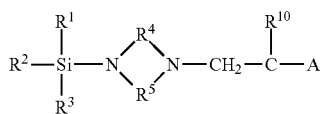
(1a)

wherein $R^1$, $R^2$, $R^3$, $R^4$, $R^5$, $R^{10}$, and A are as defined above.

When $R^{10}$ stands for a substituted or unsubstituted monovalent hydrocarbon group of 1 to 20 carbon atoms, examples of the hydrocarbon group are as illustrated above for $R^1$, $R^2$, $R^3$ and $R^9$.

Examples of the compound of formula (2) include
1-trimethylsilylimidazolidine,
1-hexyldimethylsilylimidazolidine,
1-decyldimethylsilylimidazolidine,
1-triethylsilylimidazolidine,
1-triisobutylsilylimidazolidine,
1-t-butyldimethylsilylimidazolidine,
1-t-butyldiphenylsilylimidazolidine,
1-thexyldimethylsilylimidazolidine,
1-triisopropylsilylimidazolidine,
1-tri(sec-butyl)silylimidazolidine,
1-tricyclopentylsilylimidazolidine,
1-tricyclohexylylsilylimidazolidine,
1-trimethylsilylpiperazine,
1-hexyldimethylsilylpiperazine,
1-decyldimethylsilylpiperazine,
1-triethylsilylpiperazine,
1-triisobutylsilylpiperazine,
1-t-butyldimethylsilylpiperazine,
1-t-butyldiphenylsilylpiperazine,
1-thexyldimethylsilylpiperazine,
1-triisopropylsilylpiperazine,
1-tri(sec-butyl)silylpiperazine,
1-tricyclopentylsilylpiperazine,
1-tricyclohexylylsilylpiperazine,
1-trimethylsilylhexahydropyrimidine,
1-hexyldimethylsilylhexahydropyrimidine,
1-decyldimethylsilylhexahydropyrimidine,
1-triethylsilylhexahydropyrimidine,
1-triisobutylsilylhexahydropyrimidine,
1-t-butyldimethylsilylhexahydropyrimidine,
1-t-butyldiphenylsilylhexahydropyrimldine,
1-thexyldimethylsilylhexahydropyrimidine,
1-triisopropylsilylhexahydropyrimidine,
1-tri(sec-butyl)silylhexahydropyrimidine,
1-tricyclopentylsilylhexahydropyrimidine,
1-tricyclohexylylsilylhexahydropyrimidine, etc.

Examples of the compound of formula (3) include methyl acrylate, ethyl acrylate, methyl methacrylate, ethyl methacrylate, acrylonitrile, and methacrylonitrile.

Although the compound of formula (2) and the compound of formula (3) may be used in any desired ratio, it is preferred from the standpoints of reactivity and productivity to use 0.1 to 4 moles, more preferably 0.2 to 2 moles of the compound of formula (3) per mole of the compound of formula (2).

Although the reaction temperature is not particularly limited, the preferred temperature is in the range of 0 to 200° C., especially 20 to 150° C. Although the reaction time is not particularly limited, the preferred time is 1 to 40 hours, especially 1 to 20 hours. The reaction atmosphere is preferably an inert gas atmosphere such as nitrogen or argon.

While the above reaction may run in a solventless system, a solvent may be used. Suitable solvents include hydrocarbon solvents such as pentane, hexane, cyclohexane, heptane, isooctane, benzene, toluene, and xylene; ether solvents such as diethyl ether, tetrahydrofuran and dioxane; ester solvents such as ethyl acetate and butyl acetate; aprotic polar solvents such as acetonitrile, N,N-dimethylformamide, and N-methylpyrrolidone; and chlorinated hydrocarbon solvents such as dichloromethane and chloroform, which may be used alone or in admixture of two or more.

In a further embodiment of the invention, the silyl-protected nitrogen-containing cyclic compound of formula (1) defined above may be prepared, for example, by silylating a nitrogen-containing cyclic compound of the general formula (4):

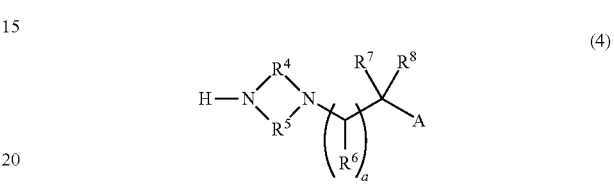
(4)

wherein $R^4$, $R^5$, $R^6$, $R^7$, $R^8$, A and a are as defined above, with a silylating agent having $R^1R^2R^3Si$— group wherein $R^1$, $R^2$ and $R^3$ are as defined above.

In formula (4), the groups represented by $R^4$, $R^5$, $R^6$, $R^7$, $R^8$, and A are as illustrated and exemplified above. Illustrative examples of the compound of formula (4) include
1-(2-methoxycarbonylethyl)imidazolidine,
1-(2-ethoxycarbonylethyl)imidazolidine,
1-(2-methoxycarbonyl-2-methylethyl)imidazolidine,
1-(2-ethoxycarbonyl-2-methylethyl)imidazolidine,
1-(2-cyanoethyl)imidazolidine,
1-(2-cyano-2-methylethyl)imidazolidine,
1-(2-methoxycarbonylethyl)piperazine,
1-(2-ethoxycarbonylethyl)piperazine,
1-(2-methoxycarbonyl-2-methylethyl)piperazine,
1-(2-ethoxycarbonyl-2-methylethyl)piperazine,
1-(2-cyanoethyl)piperazine,
1-(2-cyano-2-methylethyl)piperazine,
1-(2-methoxycarbonylethyl)hexahydropyrimidine,
1-(2-ethoxycarbonylethyl)hexahydropyrimidine,
1-(2-methoxycarbonyl-2-methylethyl)hexahydropyrimidine,
1-(2-ethoxycarbonyl-2-methylethyl)hexahydropyrimidine,
1-(2-cyanoethyl)hexahydropyrimidine,
1-(2-cyano-2-methylethyl)hexahydropyrimidine, etc.

Suitable silylating agents having $R^1R^2R^3Si$— group which can be used in the silylating reaction include triorganohalosilane compounds of the formula $R^1R^2R^3SiX$ wherein $R^1$, $R^2$ and $R^3$ are as defined above, and X is a halogen atom such as chlorine, bromine or iodine, for example, trimethylchlorosilane, trimethylbromosilane, trimethyliodosilane, triethylchlorosilane, t-butyldimethylchlorosilane, and triisopropylchlorosilane; silazane compounds of the formula: $(R^1R^2R^3Si)_2NH$ wherein $R^1$, $R^2$ and $R^3$ are as defined, above, for example, hexamethyldisilazane and hexaethyldisilazane; silylamide compounds of the formula: $CR_3C(-OSiR^1R^2R^3)=NSiR^1R^2R^3$ wherein R is hydrogen or fluorine, $R^1$, $R^2$ and $R^3$ are as defined above, for example, bis(trimethylsilyl)acetamide, bis(triethylsilyl)acetamide, and bis(trimethylsilyl) trifluoroacetamide; and sulfonic acid silyl ester compounds of the formula: $CR_3SO_3SiR^1R^2R^3$ wherein R is hydrogen or fluorine, $R^1$, $R^2$ and $R^3$ are as defined above, for example, trimethylsilyl methanesulfonate and trimethylsilyl trifluoromethanesulfonate.

Although the compound of formula (4) and the silylating agent may be used in any desired ratio, it is preferred from the standpoints of reactivity and productivity to use 1 to 4 moles, more preferably 1 to 2 moles of the silylating agent (as silyl groups) per mole of the compound of formula (4).

Although the reaction temperature is not particularly limited, the preferred temperature is in the range of 0 to 200° C. especially 20 to 150° C. Although the reaction time is not particularly limited, the preferred time is 1 to 40 hours, especially 1 to 20 hours.

A catalyst may be used in the reaction although the reaction may run without a catalyst. Suitable catalysts may be either basic or acidic compounds and include tertiary amines such as trimethylamine, triethylamine and triphenylamine; quaternary ammonium salts such as tetrabutylammonium chloride and tetrabutylammonium bromide; and acids such as sulfuric acid and sulfonic acid, derivatives thereof and inorganic salts thereof.

While the above reaction may run in a solventless system, a solvent may be used. Suitable solvents include hydrocarbon solvents such as pentane, hexane, cyclohexane, heptane, isooctane, benzene, toluene, and xylene; ether solvents such as diethyl ether, tetrahydrofuran and dioxane; ester solvents such as ethyl acetate and butyl acetate; aprotic polar solvents such as acetonitrile, N,N-dimethylformamide, and N-methylpyrrolidone; and chlorinated hydrocarbon solvents such as dichloromethane and chloroform, which may be used alone or in admixture of two or more.

EXAMPLE

Examples of the invention are given below by way of illustration and not by way of limitation.

Synthesis Example 1

1-t-butyldimethylsilylpiperazine

A flask equipped with a stirrer, reflux condenser; dropping funnel and thermometer was charged with 1076.3 g (12.5 mol) of piperazine and 500 ml of xylene and heated at 110° C. Once the internal temperature became steady, 1507.0 g (5.0 mol) of a 50 wt % toluene solution of t-butyldimethylchlorosilane was added dropwise over 3 hours. Stirring was continued for 2 hours at the temperature. The reaction solution was cooled to room temperature, to which 2,500 g of a 10 wt % sodium hydroxide aqueous solution was added. The organic layer was separated. On distillation, 646.6 g of a fraction having a boiling point of 70-71° C./0.2 kPa was collected, which was 1-t-butyldimethylsilylpiperazine.

Example 1

1-t-butyldimethylsilyl-4-(2-methoxycarbonylethyl)piperazine

A flask equipped with a stirrer, reflux condenser, dropping funnel and thermometer was charged with 160.3 g (0.8 mol) of 1-t-butyldimethylsilylpiperazine (Synthesis Example 1) and heated at 70° C. Once the internal temperature became steady, 75.8 g (0.88 mol) of methyl acrylate was added dropwise over 2 hours. Stirring was continued for 4 hours at the temperature. On distillation of the reaction solution, 219.9 g of a fraction having a boiling point of 135-137° C./0.4 kPa was collected.

Figure 2:
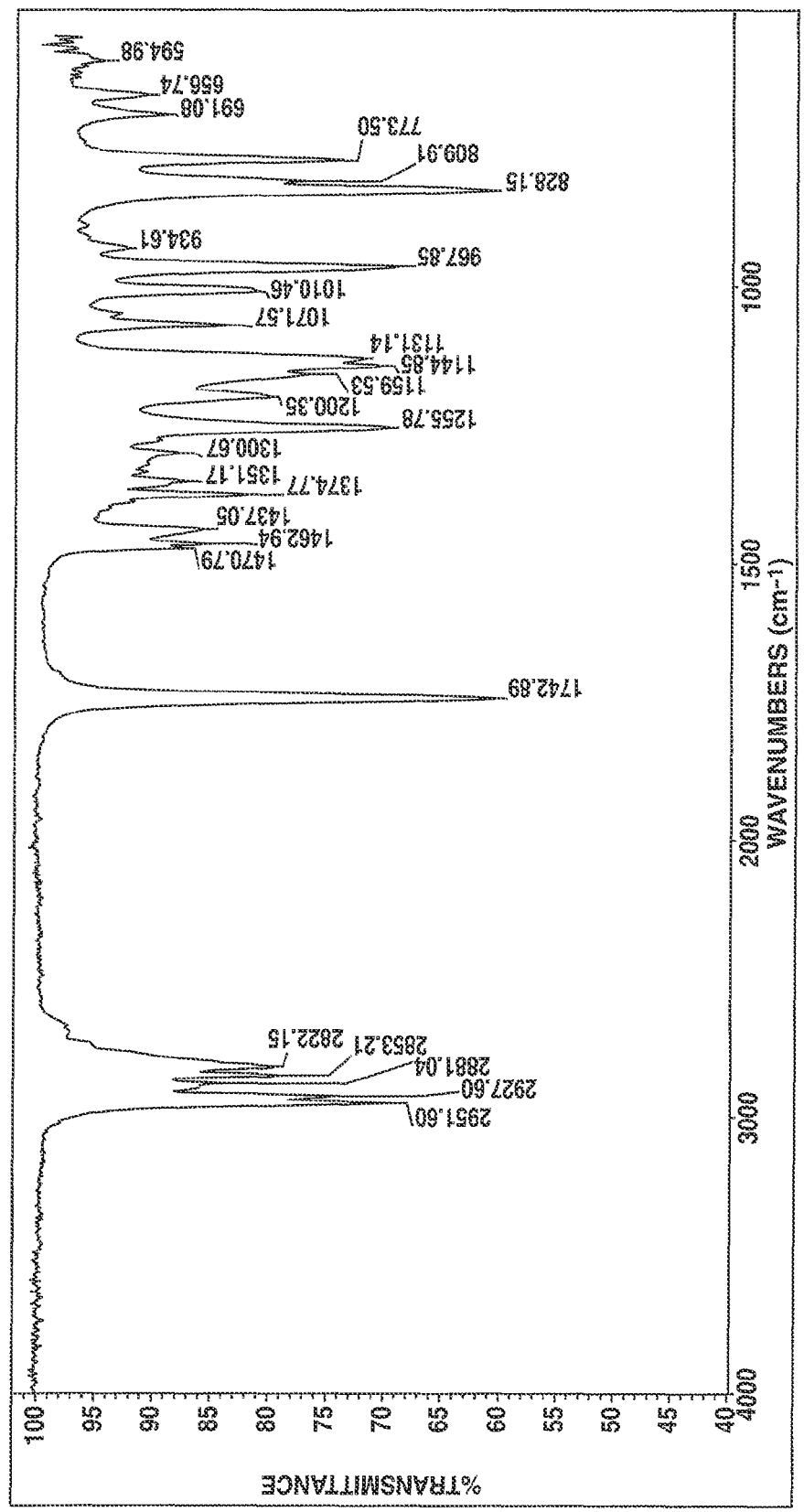
FIG. 2 is the IR spectrum of 1-t-butyldimethylsilyl-4-(2-methoxycarbonylethyl)piperazine obtained in Example 1.

The fraction was analyzed by mass, $^1$H-NMR and IR spectrometry.
MS
m/z 286, 229, 187, 89, 73, 59
$^1$H-NMR spectrum (in heavy chloroform solvent)
see FIG. 1
IR spectrum
see FIG. 2
From these analytical results, the compound was identified to be 1-t-butyldimethylsilyl-4-(2-methoxycarbonylethyl)piperazine.

Example 2

1-t-butyldimethylsilyl-4-(2-cyanoethyl)piperazine

A flask equipped with a stirrer, reflux condenser, dropping funnel and thermometer was charged with 160.3 g (0.8 mol) of 1-t-butyldimethylsilylpiperazine (Synthesis Example 1) and heated at 70° C. Once the internal temperature became steady, 46.7 g (0.88 mol) of acrylonitrile was added dropwise over 2 hours. Stirring was continued for 4 hours at the temperature. On distillation of the reaction solution, 194.1 g of a fraction having a boiling point of 145-147° C./0.4 kPa was collected.

Figure 3:
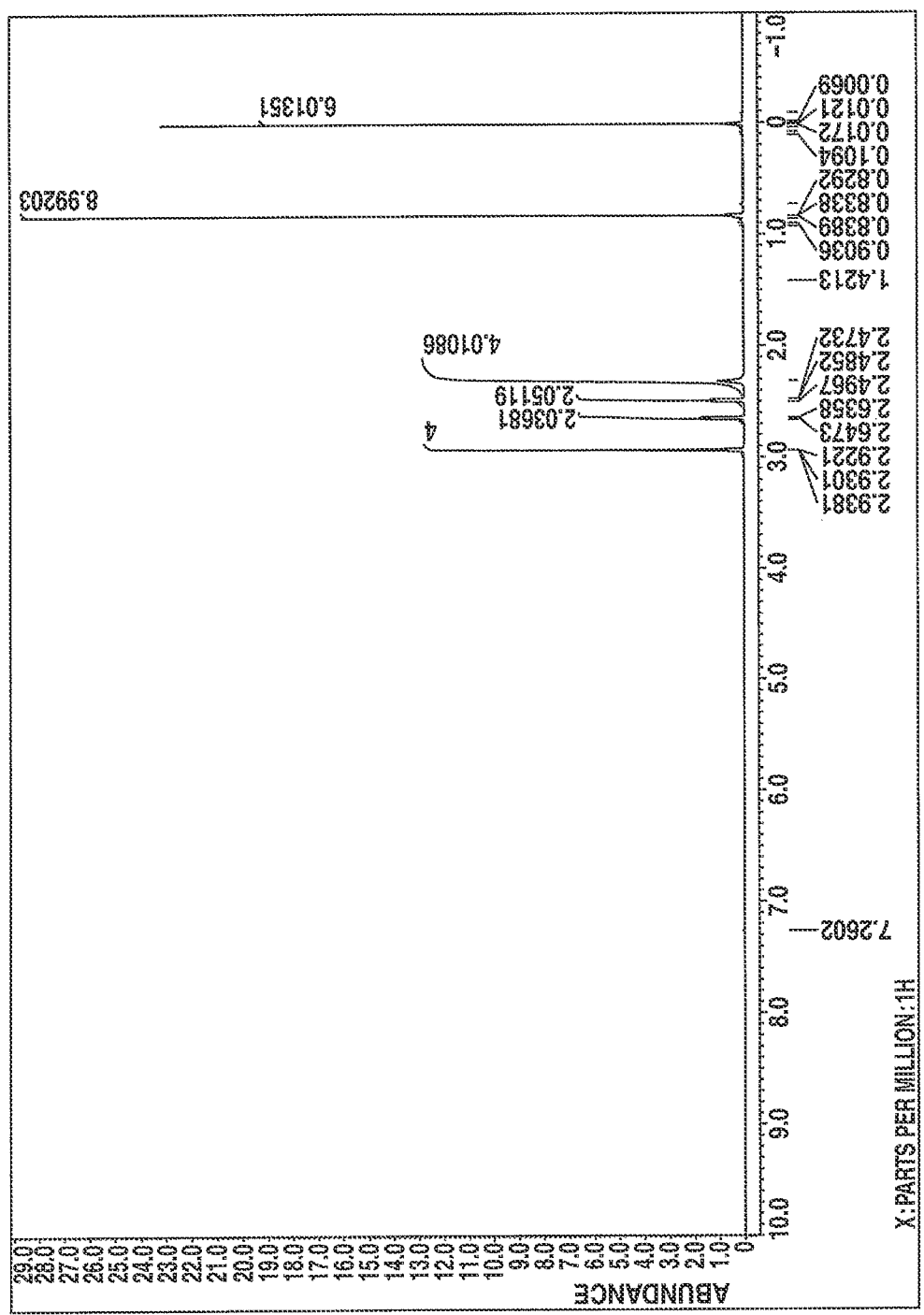
FIGS. 3 and 4 are the $^1$H-NMR and IR spectra of 1-t-butyldimethylsilyl-4-(2-cyanoethyl)piperazine obtained in Example 2, respectively.
Figure 4:
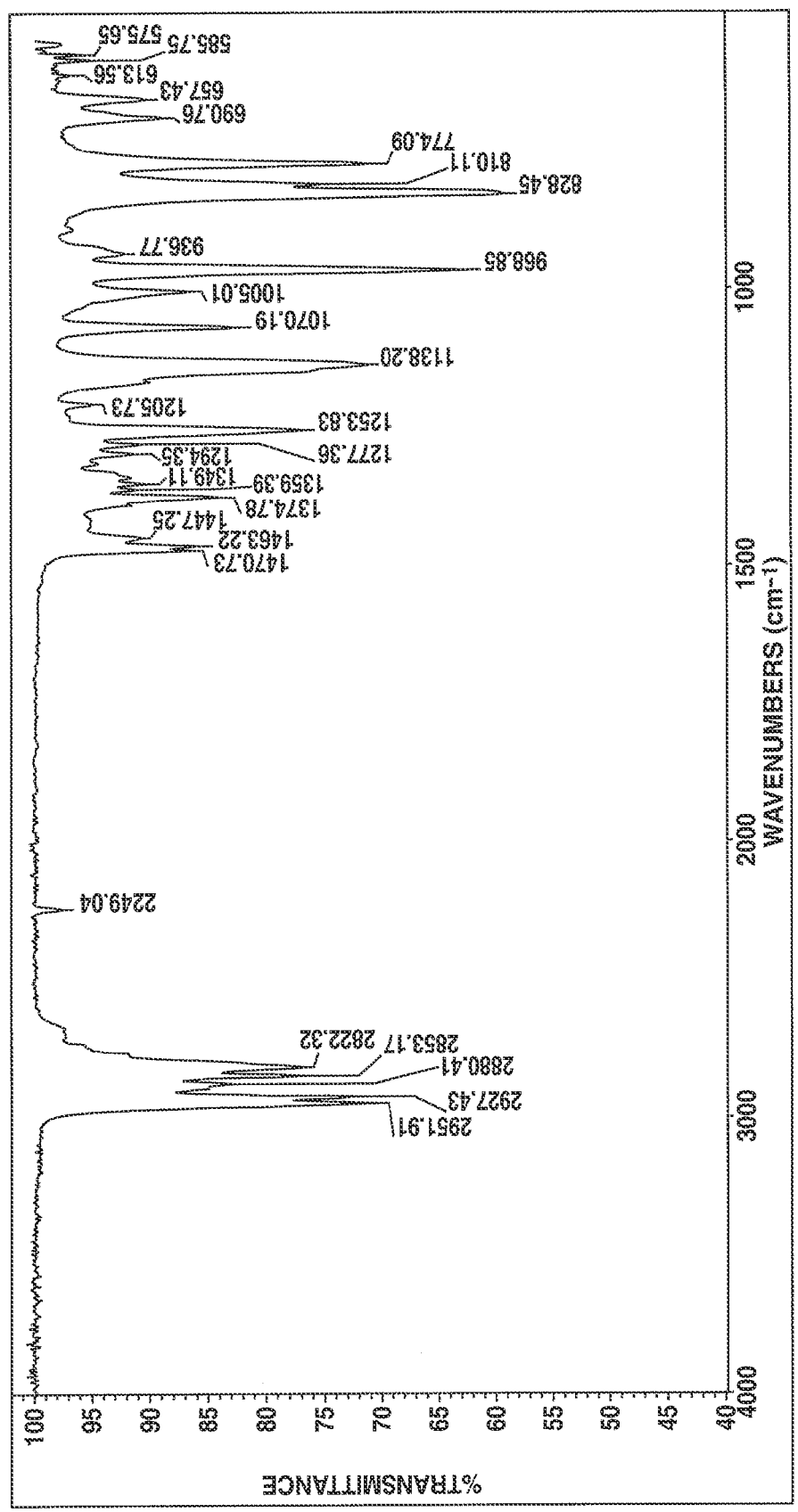

The fraction was analyzed by mass, $^1$H-NMR and IR spectrometry.
MS
m/z 253, 238, 196, 155, 73, 59
$^1$H-NMR spectrum (in heavy chloroform solvent)
see FIG. 3
IR spectrum
see FIG. 4
From these analytical results, the compound was identified to be 1-t-butyldimethylsilyl-4-(2-cyanoethyl)piperazine.

Synthesis Example 2

1-triisopropylsilylpiperazine

A flask equipped with a stirrer, reflux condenser, dropping funnel and thermometer was charged with 189.4 g (2.2 mol) of piperazine, 200 ml of xylene, and 1.0 g (0.01 mol) of methanesulfonic acid and heated at 130° C. Once the internal temperature became steady, 192.8 g (1.0 mol) of triisopropylchlorosilane was added dropwise over 2 hours. Stirring was continued for 10 hours at the temperature. The reaction solution was cooled to room temperature, to which 500 g of a 10 wt % sodium hydroxide aqueous solution was added. The organic layer was separated. On distillation, 132.6 g of a fraction having a boiling point of 109-111° C./0.4 kPa was collected, which was 1-triisopropylsilylpiperazine.

Example 3

1-triisopropylsilyl-4-(2-methoxycarbonylethyl)piperazine

A flask equipped with a stirrer, reflux condenser, dropping funnel and thermometer was charged with 194.0 g (0.8 mol) of 1-triisopropylsilylpiperazine (Synthesis Example 2) and heated at 70° C. Once the internal temperature became steady, 75.8 g (0.88 mol) of methyl acrylate was added dropwise over 2 hours. Stirring was continued for 4 hours at the temperature. On distillation of the reaction solution, 250.0 g of a fraction having a boiling point of 163-164° C./0.4 kPa was collected.

The fraction was analyzed by mass, $^1$H-NMR and IR spectrometry.

MS m/z 328, 285, 243, 198, 97, 59

Figure 5:
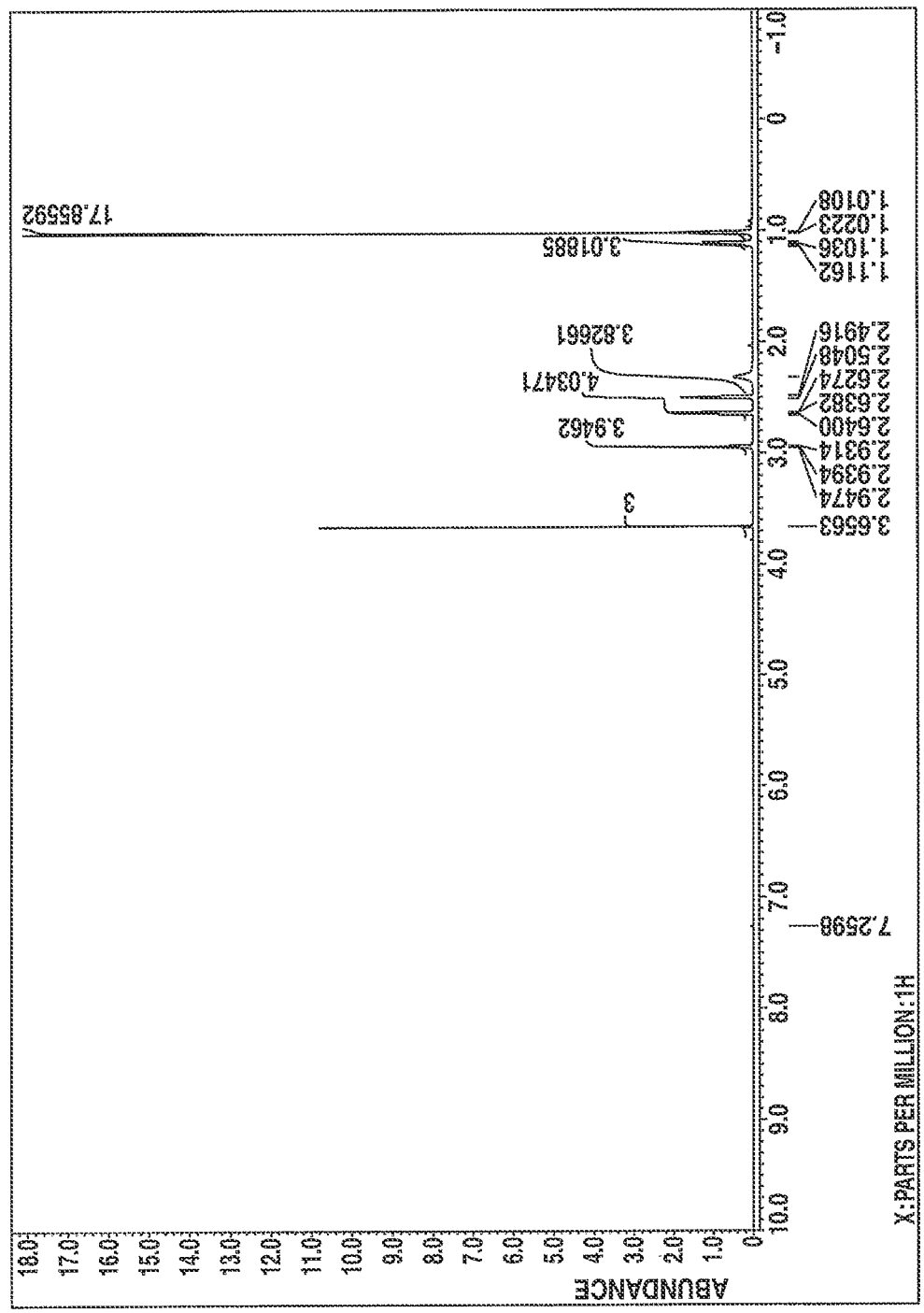
FIGS. 5 and 6 are the $^1$H-NMR and IR spectra of 1-triisopropylsilyl-4-(2-methoxycarbonylethyl)piperazine obtained in Example 3, respectively.

$^1$H-NMR spectrum (in heavy chloroform solvent)

see FIG. 5

Figure 6:
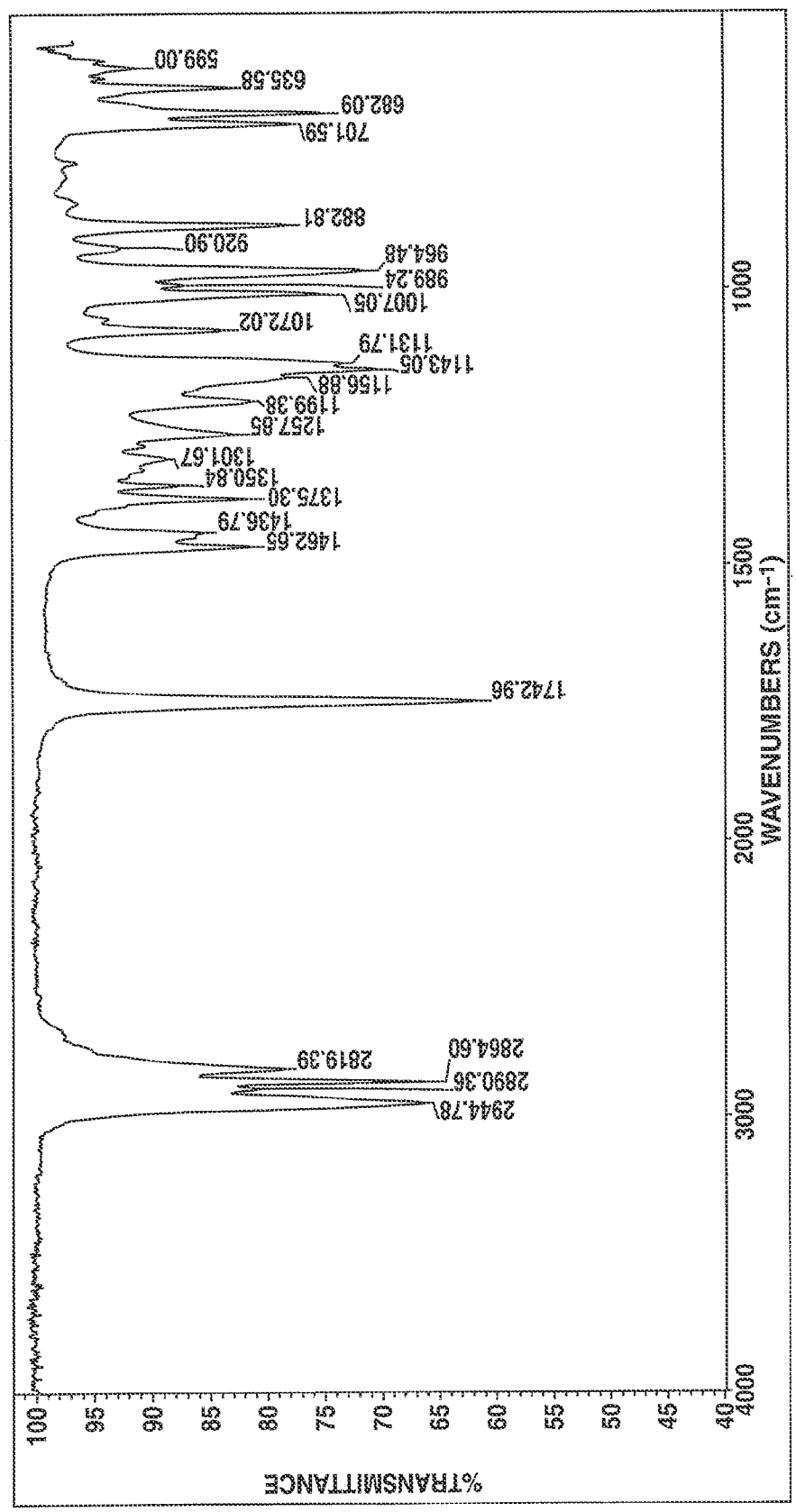

IR spectrum see FIG. 6

From these analytical results, the compound was identified to be 1-triisopropylsilyl-4-(2-methoxycarbonylethyl)piperazine.

Example 4

1-triisopropylsilyl-4-(2-cyanoethyl)piperazine

A flask equipped with a stirrer, reflux condenser, dropping funnel and thermometer was charged with 194.0 g (0.8 mol) of 1-triisopropylsilylpiperazine (Synthesis Example 2) and heated at 70° C. Once the internal temperature became steady, 46.7 g (0.88 mol) of acrylonitrile was added dropwise over 2 hours. Stirring was continued for 4 hours at the temperature. On distillation of the reaction solution, 224.8 g of a fraction having a boiling point of 179-180° C./0.4 kPa was collected.

The fraction was analyzed by mass, $^1$H-NMR and IR spectrometry.

MS m/z 295, 252, 211, 169, 97, 59

Figure 7:
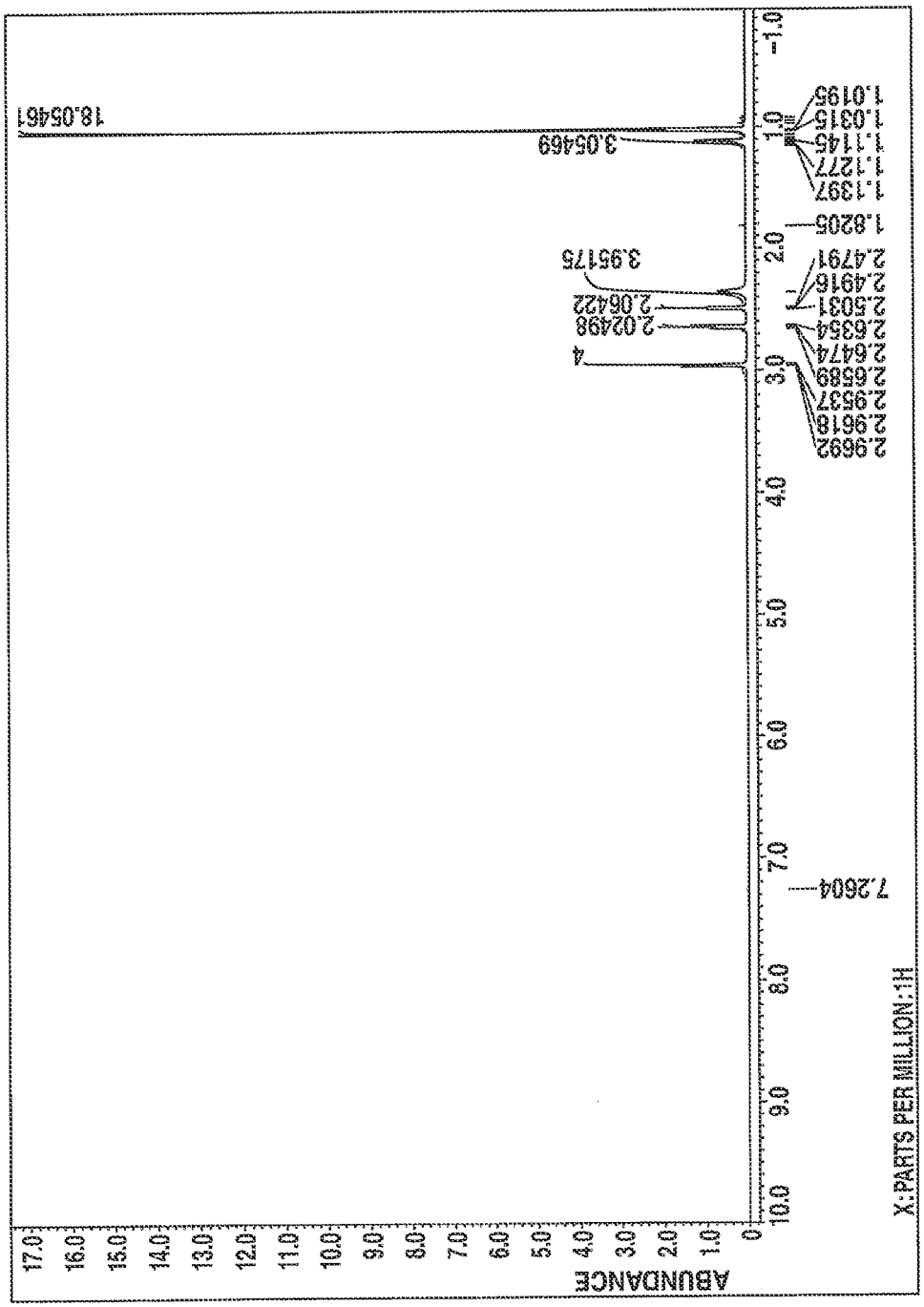
FIGS. 7 and 8 are the $^1$H-NMR and IR spectra of 1-triisopropylsilyl-4-(2-cyanoethyl)piperazine obtained in Example 4, respectively.

$^1$H-NMR spectrum (in heavy chloroform vent)

see FIG. 7

Figure 8:
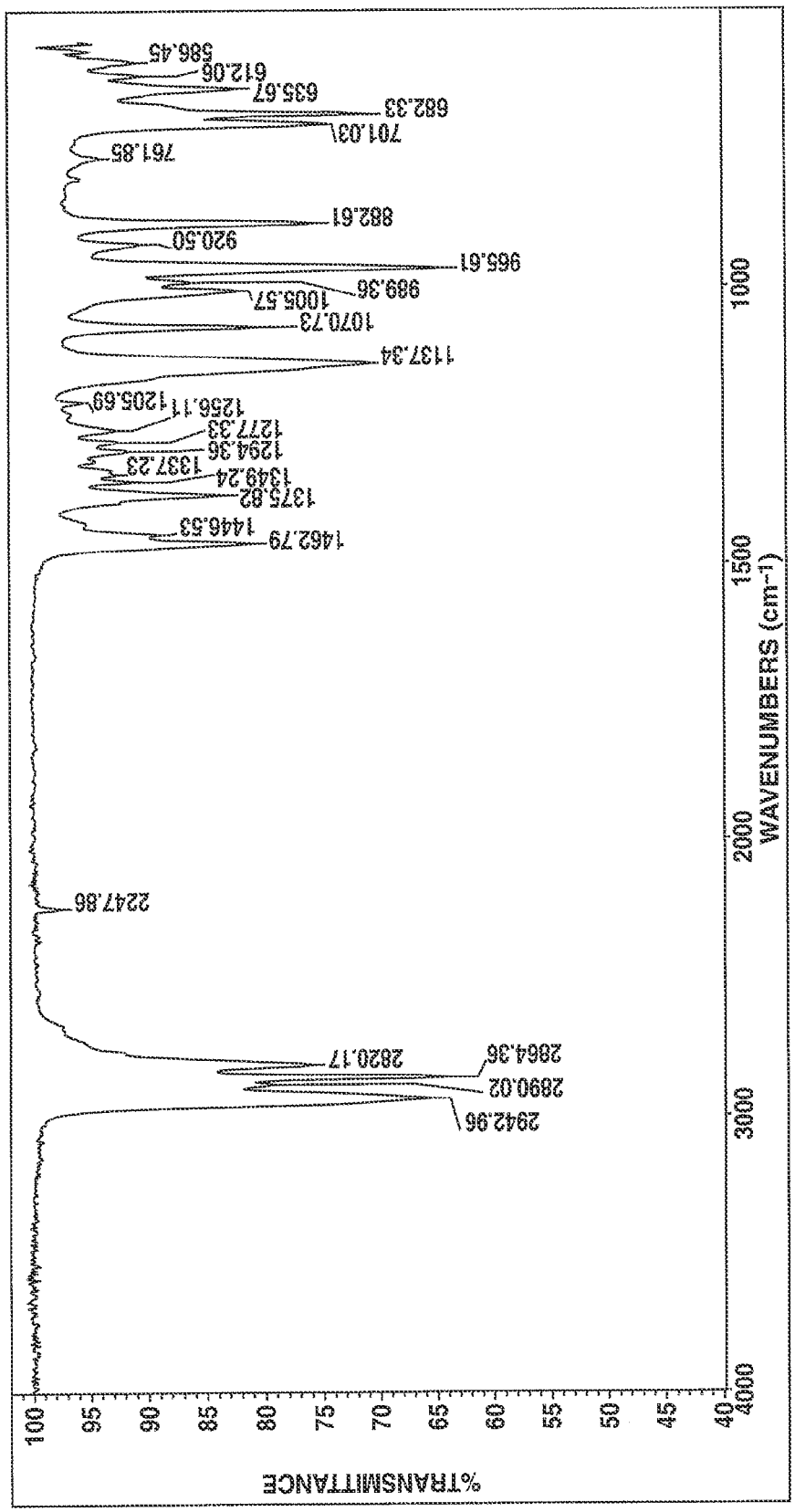

IR spectrum see FIG. 8

From these analytical results, the compound was identified to be 1-triisopropylsilyl-4-(2-cyanoethyl)piperazine.

Japanese Patent Application No. 2013-113846 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A silyl-protected nitrogen-containing cyclic compound having the formula (1):

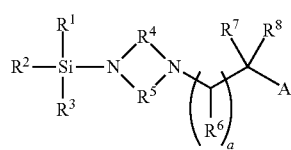

(1)

wherein $R^1$, $R^2$ and $R^3$ each are an unsubstituted monovalent hydrocarbon group of 1 to 20 carbon atoms, $R^4$ and $R^5$ each are a divalent hydrocarbon group such that the cyclic structure containing $R^4$ and $R^5$ is piperazine, and hexahydropyrimidine, $R^6$, $R^7$ and $R^8$ each are hydrogen or an unsubstituted monovalent hydrocarbon group of 1 to 20 carbon atoms, A is —C(O)OR$^9$ or —C≡N, R$^9$ is an unsubstituted monovalent hydrocarbon group of 1 to 20 carbon atoms, and a is 0 or 1.

2. The compound of claim 1 wherein $R^4$ and $R^5$ each are ethylene such that the cyclic structure containing $R^4$ and $R^5$ is piperazine.

3. A method for preparing a silyl-protected nitrogen-containing cyclic compound, comprising the step of reacting a compound of the formula (2):

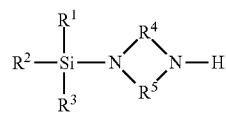

(2)

wherein $R^1$, $R^2$ and $R^3$ each are an unsubstituted monovalent hydrocarbon group of 1 to 20 carbon atoms, $R^4$ and $R^5$ each are a divalent hydrocarbon group such that the cyclic structure containing $R^4$ and $R^5$ is piperazine, and hexahydropyrimidine, with a compound of the formula (3):

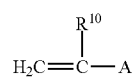

(3)

wherein $R^{10}$ is hydrogen or an unsubstituted monovalent hydrocarbon group of 1 to 20 carbon atoms, A is —C(O)OR$^9$ or —C≡N, and R$^9$ is an unsubstituted monovalent hydrocarbon group of 1 to 20 carbon atoms, thereby forming a silyl-protected nitrogen-containing cyclic compound having the formula (1a):

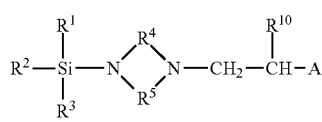

(1a)

wherein $R^1$, $R^2$, $R^3$, $R^4$, $R^5$, $R^{10}$, and A are as defined above.

4. A method for preparing a silyl-protected nitrogen-containing cyclic compound, comprising the step of silylating a nitrogen-containing cyclic compound of the formula (4):

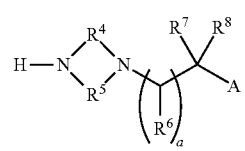

(4)

wherein $R^4$ and $R^5$ each are a divalent hydrocarbon group such that the cyclic structure containing $R^4$ and $R^5$ is piperazine, and hexahydropyrimidine, $R^6$, $R^7$ and $R^8$ each are hydrogen or an unsubstituted monovalent hydrocarbon group of 1 to 20 carbon atoms, A is —C(O)OR$^9$ or —C≡N, R$^9$ is an unsubstituted monovalent hydrocarbon group of 1 to 20 carbon atoms, and a is 0 or 1, with a silylating agent having an R$^1$R$^2$R$^3$Si— group wherein $R^1$, $R^2$ and $R^3$ each are an unsubstituted monovalent hydrocarbon group of 1 to 20 carbon atoms, thereby forming a silyl-protected nitrogen-containing cyclic compound having the formula (1):

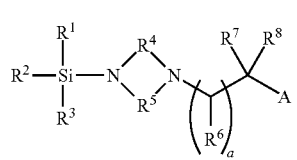
(1)
wherein $R^1$, $R^2$, $R^3$, $R^4$, $R^5$, $R^6$, $R^7$, $R^8$, A, and a are as defined above.
* * * * *